US006965792B2

(12) United States Patent
Avrin et al.

(10) Patent No.: US 6,965,792 B2
(45) Date of Patent: Nov. 15, 2005

(54) SUSCEPTOMETERS FOR FOREIGN BODY DETECTION

(75) Inventors: William F. Avrin, San Diego, CA (US); Sankaran Kumar, San Marcos, CA (US); Peter V. Czipott, San Diego, CA (US); Richard J. McClure, San Diego, CA (US); R. Kemp Massengill, Leucadia, CA (US)

(73) Assignees: MedNovus, Inc., Leucadia, CA (US); Quantum Magnetics, Inc., San Diego, CA (US)

( * ) Notice: Subject to any disclaimer, the term of this patent is extended or adjusted under 35 U.S.C. 154(b) by 670 days.

(21) Appl. No.: 10/025,191

(22) Filed: Dec. 18, 2001

(65) Prior Publication Data

US 2002/0151779 A1    Oct. 17, 2002

Related U.S. Application Data

(63) Continuation-in-part of application No. 09/741,774, filed on Dec. 15, 2000, now Pat. No. 6,418,335, which is a continuation of application No. 09/135,890, filed on Aug. 18, 1998, now Pat. No. 6,208,884, which is a continuation-in-part of application No. 08/670,393, filed on Jun. 25, 1996, now Pat. No. 5,842,986, said application No. 10/025,191 is a continuation-in-part of application No. 09/818,700, filed on Mar. 27, 2001, which is a continuation-in-part of application No. 09/135,890, filed on Aug. 18, 1998, now Pat. No. 6,208,884, said application No. 10/025,191.

(60) Provisional application No. 60/316,942, filed on Sep. 1, 2001, provisional application No. 60/272,873, filed on Mar. 2, 2001, provisional application No. 60/281,120, filed on Apr. 3, 2001.

(51) Int. Cl.$^7$ .............................................. A61B 5/05
(52) U.S. Cl. .................... 600/407; 600/409; 600/410; 324/307

(58) Field of Search ................................ 600/407, 408, 600/409, 425, 433, 300, 11, 410; 324/201, 324/294, 248, 207.16, 307; 505/162; 174/262; 29/845; 604/294

(56) References Cited

U.S. PATENT DOCUMENTS 3,656,481 A  *  4/1972  Ness .......................... 600/11

(Continued)

FOREIGN PATENT DOCUMENTS

DE          4436078        4/1996

(Continued)

OTHER PUBLICATIONS

Avrin, W.; *Improved Nondestructive Evaluation of Deep, Inaccessible Flaws in Metal Structures;* National Science Foundation Phase I final Report; pp. 1-29; Dec., 1995.

(Continued)

Primary Examiner—Eleni Mantis Mercader
Assistant Examiner—Baisakhi Roy
(74) Attorney, Agent, or Firm—Gerald W. Spinks (57)         ABSTRACT

Methods and apparatus for minimizing the effects of temperature drift in a magnetic susceptibility measurement instrument, such as an instrument used in pre-MRI screening for the presence of ferromagnetic foreign bodies. The magnetic field source and magnetic sensors can be combined into a single, rigid unit. The stability and sensitivity required in high quality magnetic susceptibility measurements can be achieved through symmetrical design of the source-sensor unit, minimization of thermal stresses, minimization of temperature variations, use of materials with low thermal expansion coefficients, or through appropriate combinations thereof. Use of patient eye movement where an eye is being screened, use of a water bag between the patient and the instrument, or use of telemedicine to facilitate performance of the necessary computations can also be incorporated.

3 Claims, 5 Drawing Sheets

U.S. PATENT DOCUMENTS

| | | | |
|---|---|---|---|
| 3,660,726 A * | 5/1972 | Ammon et al. | 174/262 |
| 4,042,876 A * | 8/1977 | Visioli, Jr. | 324/207.16 |
| 4,431,005 A * | 2/1984 | McCormick | 600/433 |
| 4,588,947 A * | 5/1986 | Ketchen | 324/201 |
| 4,709,213 A | 11/1987 | Padhrasky | |
| 4,801,882 A | 1/1989 | Daalmans | |
| 4,827,217 A * | 5/1989 | Paulson | 600/409 |
| 4,837,489 A | 6/1989 | McFee | |
| 4,969,469 A | 11/1990 | Mills | |
| 5,057,095 A | 10/1991 | Fabian | |
| 5,081,071 A * | 1/1992 | Hirschkoff | 600/409 |
| 5,099,845 A | 3/1992 | Besz et al. | |
| 5,105,829 A | 4/1992 | Fabian et al. | |
| 5,107,862 A | 4/1992 | Fabian et al. | |
| 5,172,472 A * | 12/1992 | Lindner et al. | 29/845 |
| 5,188,126 A | 2/1993 | Fabian et al. | |
| 5,190,059 A | 3/1993 | Fabian et al. | |
| 5,233,992 A | 8/1993 | Holt et al. | |
| 5,268,165 A | 12/1993 | Hedlund et al. | |
| 5,305,751 A | 4/1994 | Chopp et al. | |
| 5,322,682 A | 6/1994 | Bartzokis et al. | |
| 5,353,807 A | 10/1994 | DeMarco | |
| 5,384,109 A | 1/1995 | Klaveness et al. | |
| 5,408,178 A | 4/1995 | Wikswo et al. | |
| 5,425,382 A | 6/1995 | Golden et al. | |
| 5,456,718 A | 10/1995 | Szymaitis | |
| 5,469,056 A | 11/1995 | Eschner et al. | |
| 5,494,033 A * | 2/1996 | Buchanan et al. | 600/409 |
| 5,494,035 A * | 2/1996 | Leuthold et al. | 600/409 |
| 5,509,412 A | 4/1996 | Bahn | |
| 5,524,086 A * | 6/1996 | Kiyuna et al. | 600/408 |
| 5,546,943 A * | 8/1996 | Gould | 600/425 |
| 5,558,091 A | 9/1996 | Acker et al. | |
| 5,610,518 A | 3/1997 | Chamberlain, IV | |
| 5,619,991 A * | 4/1997 | Sloane | 600/300 |
| 5,686,836 A | 11/1997 | Sasada et al. | |
| 5,689,184 A | 11/1997 | Jeffers et al. | |
| 5,705,924 A | 1/1998 | Jeffers | |
| 5,709,225 A | 1/1998 | Budgifvars et al. | |
| 5,735,279 A | 4/1998 | Klaveness et al. | |
| 5,757,183 A | 5/1998 | Smith et al. | |
| 5,957,847 A | 9/1999 | Minakuchi et al. | |

FOREIGN PATENT DOCUMENTS

| | | |
|---|---|---|
| EP | 0481211 | 4/1992 |
| EP | 0695531 | 7/1996 |
| GB | 2204133 | 11/1988 |
| GB | 2262606 | 6/1993 |
| WO | WO96/05768 | 2/1996 |

OTHER PUBLICATIONS

Avrin, W.; *Magnetoresistive Eddy-Current Sensor for Detecting Deeply Buried Flaws;* Progress in Quantitative Nondestructive Evaluation, vol. 15; Proceedings of Conference in Seattle; pp. 1-6; Jul. 30-Aug. 4, 1995.

Bastuscheck, C.M.; *Technique for Measuring the AC Susceptibility of Portions of the Human Body or Other Large Objects;* J. Appl. Phys. 58(10), pp. 3896-3906, Nov., 1985.

Brittenham, Gary M., et al.; *Hepatic Iron Stores and Plasma Ferritin Concentration in Patients With Sickle Cell Anemia and Thalassemia Major;* American Journal of Hematology; Jul. 23, 1992; pp. 81-85; vol. 42; Wiley-Liss, Inc.

Brittenham, Gary M., et al.; *Magnetic-Susceptibility Measurement of Human Iron Stores;* The New England Journal of Medicine; Dec. 30, 1982; pp. 1671-1675; vol. 307 No. 27.

Bryden, F.M.; *Real Time Ultrasound in the Assessment of Intraocular Foreign Bodies;* Eye 4, pp. 727-731; (1990).

Costa Monteiro, E.; *Magnetic Measurement Techniques for Locating Foreign Bodies in Humans;* Tenth International Conference on Biomagnetism, p. 314 (1996).

Farrell, et al., *Magnetic Measurement of Human Iron Stores,* IEEE Transactions on Magnetics, vol. MAG-16, No. 5, pp. 818-823, (1980).

Finn, E.J., *Ferromagnetic Materials in Patients: Detection Before MR Imaging;* Radiology 156, pp. 139-141 (1985).

Fischer, R. et al.; *Liver Iron Quantification in the Diagnosis and Therapy Control of Iron Overload Patients;* Biomagnetism Clinical Aspects; 1992; pp. 585-588; Elsevier Science Publishers.

Fischer, R., et al.; *The Calibration Problem in Liver Iron Susceptometry;* Advances in Biomagnetism; date unknown; pp. 501-504.

Greenblatt, R.E.; *Probabilistic Reconstruction of Multiple Sources in the Bioelectromagnetic Inverse Problem;* Inverse Problems 9, pp. 271-284 (1992).

Kanal, E.; *Aneurysm Clip Testing for Ferromagnetic Properties: Clip Variability Issues;* Radiology, pp. 576-578; (1995).

Mentor Corporation; *The Detector, Injection Port Detection System;* Brochure, 6 pp. (1996).

Paulson, D.N.; *Biomagnetic Susceptometer with SQUID Instrumentation;* IEEE Transaction on Magnetics, vol. 27; No. 2; pp. 3249-3252.

Paulson, D.N.; *The Hamburg Biosusceptometer for Liver Iron Quantification;* Advances in Biomagnetism; pp. 497-500;, date unknown.

Scholz, B., et al.; *Probability-Based Current Dipole Localization from Biomagnetic Fields;* IEEE Transactions on Biomedical Engineering; vol. 41, No. 8; pp. 735-742; Aug., 1993.

Sekihara, K., et al.; *Reduction of Brain Noise Influence in Evoked Neuromagnetic Source Localization Using Noise Spatial Correlation;* Phys. Med. Biol. 39; pp. 937-946; ).

Sepulveda, N., et al.; *Magnetic Susceptibility Tomography for Three-Dimensional Imaging of Diamagnetic and Paramagnetic Objects;* IEEE Transactions on Magnetics, vol. 30; No. 6; pp. 5062-5069; (1993).

Shellock, F.G.; *Magnetic Resonance;* Bioeffects, Safety and Patient Management; pp. 115-126; (1996).

Smith, N.; *A High-Sensitivity Magnetoresistive Magnetometer;* J. Appl. Phys. 69 (8); pp. 5052-5084; (1991).

Scholz, B., *Probability-Based Current Dipole Localization from Biomagnetic Fields,* IEEE Transactions on Biomedical Engineering, vol. 41, No. 8, pp. 735-742, (1993).

Wynn, W.M.; *Advanced Superconducting Gradiometer/ Magnetometer Arrays and a Novel Signal Processing Technique;* IEEE Transactions on Magnetics; vol. MAG-11; No. 2; pp. 701-707; (1974).

Thomas, I.M., et al.; *Spatial Resolution and Sensitivity of Magnetic Susceptibility Imaging;* IEEE Transactions on Applied Superconductivity, vol. 3, No. 1, (1992).

* cited by examiner

SUSCEPTOMETERS FOR FOREIGN BODY DETECTION

CROSS REFERENCE TO RELATED APPLICATIONS

This is a continuation-in-part patent application of U.S. patent application Ser. No. 09/741,774, filed on Dec. 15, 2000 now U.S. Pat. No. 6,418,335, and entitled "Ferromagnetic Foreign Body Detection Using Magnetics", which is a continuation patent application of U.S. patent application Ser. No. 09/135,890, filed on Aug. 18, 1998, and entitled "Noninvasive Room Temperature Instrument to Measure Magnetic Susceptibility Variations in Body Tissue", now U.S. Pat. No. 6,208,884, which was a continuation-in-part application of U.S. patent application Ser. No. 08/670,393, filed on Jun. 25, 1996, and entitled "Ferromagnetic Foreign Body Screening Method and Apparatus", now U.S. Pat. No. 5,842,986, the disclosures of which are incorporated herein by reference. This is also a continuation-in-part patent application of co-pending U.S. patent application Ser. No. 09/818,700, filed on Mar. 27, 2001, and entitled "Simplified Water Bag Technique for Magnetic Susceptibility Measurements on the Human Body and Other Specimens", which is a continuation-in-part patent application of U.S. patent application Ser. No. 09/135,890, filed on Aug. 18, 1998, and entitled "Noninvasive Room Temperature Instrument to Measure Magnetic Susceptibility Variations in Body Tissue", now U.S. Pat. No. 6,208,884, the disclosures of which are incorporated herein by reference. This application also relies upon the priority of U.S. Provisional Pat. App. Ser. No. 60/316,942, filed on Sep. 1, 2001, and entitled "Non-Reciprocating Susceptometers for Foreign Body Detection", and U.S. Provisional Pat. App. Ser. No. 60/272,873, filed on Mar. 2, 2001, and entitled "Embedded Ferromagnetic Particle Detection Apparatus and Method"; and U.S. Provisional Pat. App. No. 60/281,120, filed on Apr. 3, 2001, and entitled "Ferromagnetic Foreign Body Detection Utilizing Eye Movement".

STATEMENT REGARDING FEDERALLY SPONSORED RESEARCH OR DEVELOPMENT

The U.S. Government has a paid-up license in this invention as provided for by the terms of Grant Nos. 1 R43 EY11570-01 and 2 R44 EY11570-02A1, and Contract Nos. N43-DK-7-2250 and N44-DK-9-2309, all awarded by the National Institutes of Health.

BACKGROUND OF THE INVENTION

1. Field of the Invention

The present invention is in the field of magnetic susceptometers, especially those intended for use in ferromagnetic foreign body (FFB) detection as a safety measure prior to magnetic resonance imaging (MRI).

2. Background Art

Ultra-sensitive magnetic susceptibility measurements are useful in a number of applications, including the measurement of iron concentrations in the liver and the detection of ferromagnetic foreign bodies in the eye and brain, and elsewhere in the body, prior to magnetic resonance imaging. In the magnetic susceptibility measurement, a magnetic field is applied to a specimen, and a magnetic sensor measures the change in magnetic field due to the magnetization induced in the specimen by the applied field. The main challenge in such measurements is not only that the magnetic field response of the sample is small in absolute terms, but that the response may be many orders of magnitude smaller than the magnetic field that is applied to the specimen. Measuring such a small response, in the presence of such a relatively large applied field, is especially difficult in a room-temperature instrument, because temperature fluctuations may distort the geometrical relationship between the magnets or coils that produce the applied magnetic field and the magnetic-field sensors that detect the response of the specimen. This geometrical distortion causes fluctuations in the measured magnetic field, which can mask the desired magnetic field response of the specimen. One way to minimize such temperature drifts is to modulate the distance or spatial relationship between the specimen and the instrument, modulating the magnetic susceptibility response of the specimen at a frequency that is relatively high compared with the typically slow time-scale of the temperature drifts.

An alternative approach in sensitive magnetic susceptibility measurements is to maintain a desired geometrical relationship between the magnetic-field source(s) and the magnetic-field sensors, so as to minimize fluctuations in the measured magnetic field. The required dimensional stability of the sensor unit is determined by the required resolution of the magnetic susceptibility measurement. Certain specific applications, such as detection of ferromagnetic foreign bodies prior to MRI imaging, require resolution of changes in magnetic field that are $10^7$ or even $10^8$ times smaller than the field applied to the specimen. In order to resolve signals $10^7$ times smaller than the applied field, it would be necessary for all the relative dimensions of the sensor unit to remain constant to roughly one part in $10^7$. Some existing magnetic susceptometers, based upon superconducting quantum interference devices (SQUIDs), achieve the required stability by placing the magnetic field source or sources and magnetic field sensor or sensors in a liquid helium bath. With this approach, thermal expansion is not a problem because temperature fluctuations are controlled by the liquid-helium bath, and because the thermal expansion of most materials is essentially frozen out at liquid-helium temperatures. This geometrical stability, and not any intrinsic property of superconductors, may in fact be the single greatest advantage of working at liquid-helium temperatures. Achieving similar stability at room temperature is a significant problem.

Even if the aforementioned problems can be solved, there are additional problems related to the use of magnetic susceptibility measurements in pre-MRI screening for FFBs, including masking of the magnetic susceptibility response of the FFB by magnetic susceptibility signals from tissues in the patient's head, and masking of the magnetic susceptibility response of the FFB by the very large response due to the magnetic susceptibility contrast between the body tissues and the surrounding air. Further, the computer equipment used in interpreting the signals measured by the magnetic susceptibility instrument can add to the cost of pre-MRI screening.

BRIEF SUMMARY OF THE INVENTION

The present disclosure describes several techniques which minimize the effects of temperature drift, without modulation of the sensor-sample distance, and without relying on phenomena or materials properties which occur only at cryogenic temperatures. A first step in maintaining this geometrical relationship is to combine the magnetic field source, or sources, and the magnetic sensor, or sensors, into a single, rigid unit, which will be called the source-sensor unit throughout the discussion below.

The present invention achieves the stability and sensitivity required in high quality magnetic susceptibility measurements, and makes the high quality magnetic susceptibility measurements widely available, specifically concerning such measurements for pre-MRI screening, by the following means:

1. Exploiting symmetry;
2. Minimizing thermal stresses;
3. Minimizing temperature variations;
4. Using materials with low thermal expansion coefficients;
5. Using eye movement to enhance the sensitivity of the instrument;
6. Using a bag of deformable material to enhance the sensitivity of the instrument; and
7. Using telemedicine to make the enhanced measurements widely available and to facilitate quality control in the interpretation of test results.

The novel features of this invention, as well as the invention itself, will be best understood from the attached drawings, taken along with the following description, in which similar reference characters refer to similar parts, and in which:

DETAILED DESCRIPTION OF THE INVENTION

The features of several exemplary embodiments of the apparatus and methods of the present invention will now be described.

Exploiting symmetry in source-sensor unit configuration. One way to minimize the effects of thermal drifts in sensitive magnetic susceptibility measurements is to arrange the applied-field generating elements and magnetic sensors in a manner that (1) the signal due to the applied field is cancelled out and (2) the entire source-sensor unit is symmetrical, in such a way that the cancellation of the applied-field signal is preserved if the entire structure expands and contracts uniformly.

Figure 1:
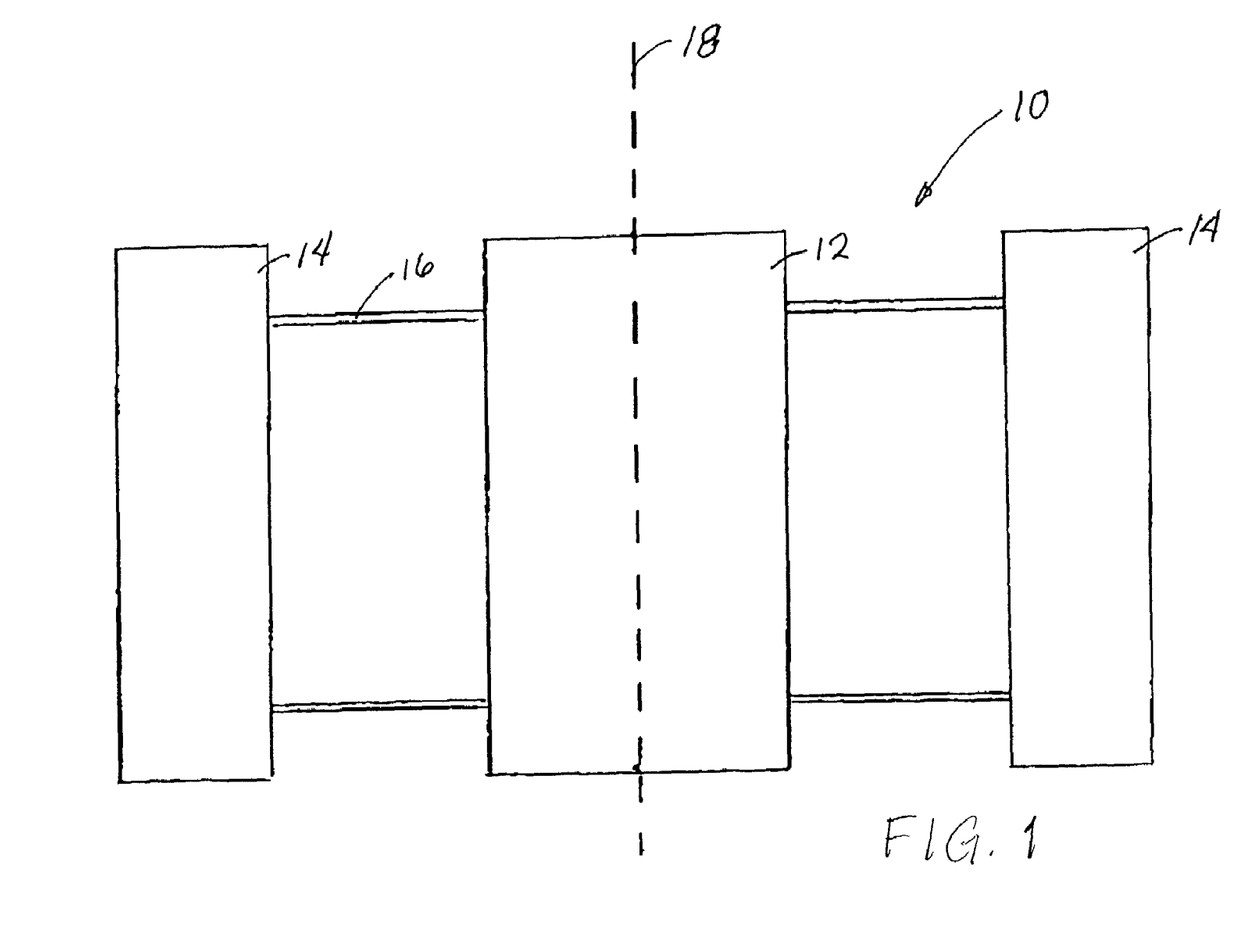
FIG. 1 is a schematic view of a source-sensor unit according to the present invention, with symmetrically disposed sensor coils.

One example of this concept is shown in FIG. 1. In this preferred embodiment, the source-sensor unit 10 consists of an applied-field coil 12 and two identical sensor coils 14, co-axially wound on a single coil form 16, with the applied-field coil 12 centered between the two sensor coils 14. The sensor coils 14 are connected in series opposition to form a first-order magnetic gradiometer. Since the sensor coils 14 are symmetrically disposed with respect to the applied-field coil 12, this gradiometer arrangement cancels the signal due to the applied field. This cancellation is maintained even if the source-sensor unit 10 expands or contracts, as long as the amount of expansion or contraction is the same throughout the structure, or is at least symmetrical with respect to the plane of mirror symmetry 18 of the coil set. As a result, the error due to an overall change in temperature, or a temperature change that is symmetrical with respect to the plane of mirror symmetry 18, is greatly reduced.

As an alternative, the applied field coil and sensor coils can be built in such a manner that the source-sensor unit configuration may not be geometrically symmetrical, but, if the thermal expansion or contraction of the structure is uniform throughout, then the applied field signal cancellation is still maintained.

Figure 2:
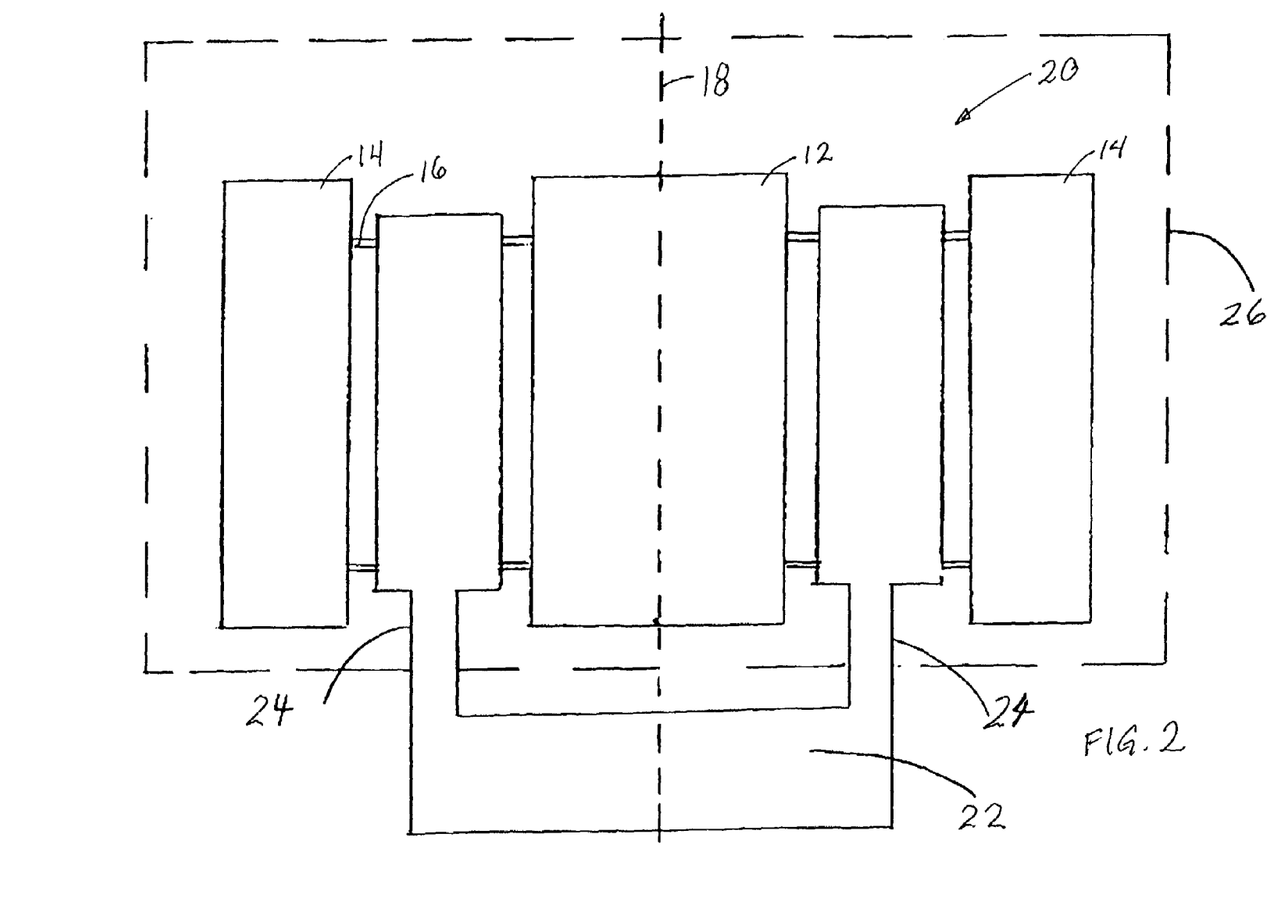
FIG. 2 is a schematic view of a source-sensor unit according to the present invention, with symmetrically disposed sensor coils and a symmetrically disposed heat sink.

In order to enhance the symmetry effect, it is desirable to maximize the thermal conductance between different parts of the structure, thus maintaining as much thermal uniformity as possible. It is also desirable to protect the source-sensor unit from ambient air currents, or to insulate it from ambient temperature changes, thus minimizing any thermal loads that may differ between different parts of the structure. It is desirable for any thermal links to the outside world, such as those required to remove the heat generated in the applied-field coil, to have the same symmetry as the source-sensor unit itself. An example of this concept is shown in the source-sensor unit 20 of FIG. 2, where, as before, an applied-field coil 12 and two identical sensor coils 14 are co-axially wound on a single coil form 16, with the applied-field coil 12 centered between the two sensor coils 14. In this embodiment, however, two thermally conductive links 24 to a heat sink 22 are placed symmetrically with respect to the plane of mirror symmetry 18 of the coil set. This symmetrical arrangement ensures that even if the temperature of the source-sensor unit 20 changes, the temperature distribution will remain symmetrical with respect to the plane of mirror symmetry 18 of the source-sensor unit 20. The source-sensor unit 20 can also be encased in a thermally insulating enclosure 26.

Figure 3:
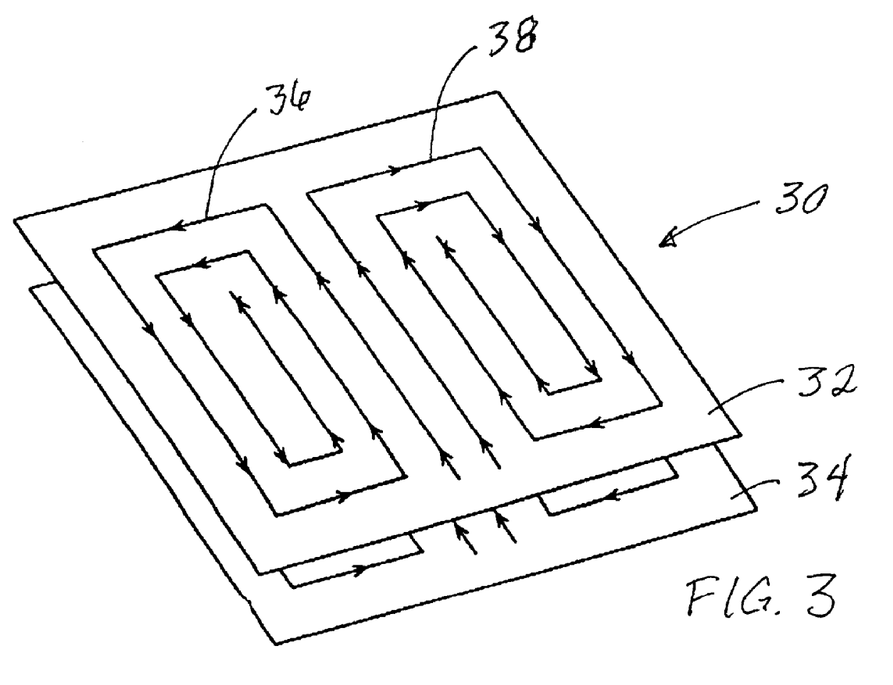
FIG. 3 is a perspective view of a source-sensor unit according to the present invention, with sensors sandwiched between parallel circuit board field coils.

FIG. 3 shows another embodiment of a source-sensor unit 30 which also uses symmetry to maintain cancellation of the applied field. One or more magnetic sensors (not shown in this view) are sandwiched between two printed circuit boards 32, 34. The central region of each circuit board 32, 34 contains a number of parallel, evenly spaced traces 36, 38 which are connected in series and carry identical currents. This arrangement approximates the effect of a uniform sheet of current in a region near the center of each board 32, 34, with return paths completing the circuit along both edges. The two circuit boards 32, 34 are connected in series, so that the currents are identical in both boards, and flow in the same direction. With this configuration of currents, the magnetic fields from the two circuit boards 32, 34 reinforce each other in the region just outside either board, but cancel each other in the region between the two circuit boards.

With this coil system, the applied field at the magnetic sensors is nulled by balancing the fields from two identical structures such as the two circuit boards 32, 34 in FIG. 3, with identical thermal time constants, and identical ohmic heat loads. With this structure, although the overall temperature of the unit 30 may vary, the changes in temperature and the resulting thermal expansion or contraction will tend to be the same for both printed circuit boards 32, 34, so that the cancellation of the applied field at the magnetic sensors is preserved.

In such a structure, it is acceptable for the overall temperature to fluctuate somewhat, as long as the whole system expands and contracts uniformly. This means that geometrical relationships are kept constant. If the field at the sensors is $10^3$ times smaller than that in the sensed region, an overall expansion of the coil system of one part in $10^5$ still will allow detection of signals $10^8$ times smaller than the field applied to the sensed region. In copper, this amount of expansion corresponds to a temperature fluctuation of one-half of a kelvin degree, which is an easy temperature range to maintain over the short time that the pre-MRI measurement will take.

The same principles of symmetry can be applied to various sensor designs, using a variety of geometries, using any type of magnetic sensor, whether the applied field is produced using permanent magnets, coils, or a combination of coils and magnetic materials.

A similar effect can be obtained by using other embodiments. For instance, two or more applied field coils which are symmetrical in their thermal properties can be symmetrically arranged so that thermal expansion or contraction of the structure preserves the symmetry that maintains the cancellation of the magnetic field in a desired location.

Minimizing thermal stresses. Differential expansion can create strains in the structure of the coil system. Such distortions can be minimized by balancing the thermal stresses. For example, if the field coils are put on printed circuit boards, it would be beneficial to put identical layers of metal, such as copper, on both sides of the board to balance out any stresses due to the differential expansion of the metal and the non-metallic substrate, such as fiberglass, of the printed circuit boards.

In addition, thermal stresses may be minimized by making all parts of the coil structure, including the coils themselves and any supporting structures, of materials that have the same thermal expansion coefficients. For example, G-10 or FR-4 fiberglass and copper are materials with a reasonably good match of thermal expansion coefficients.

One configuration which minimizes both temperature non-uniformity and thermal stresses is an applied-field coil constructed almost entirely of bars of rigid metal, such as copper, with only small insulating spacers to separate the different conductors in the coil. In this configuration, the high thermal conductivity of the metal bars would minimize temperature imbalances within the structure. In addition, thermal stresses are minimized by constructing the coil almost entirely of the same material. As a result, the basic shape of the coil is preserved, even if the overall temperature of the structure varies. If the coil is configured to cancel the magnetic field at a particular location, this field cancellation would be insensitive to variations in temperature. A low-drift magnetic susceptometer is then created by placing a magnetic sensor at the location of field cancellation.

Figure 4A:
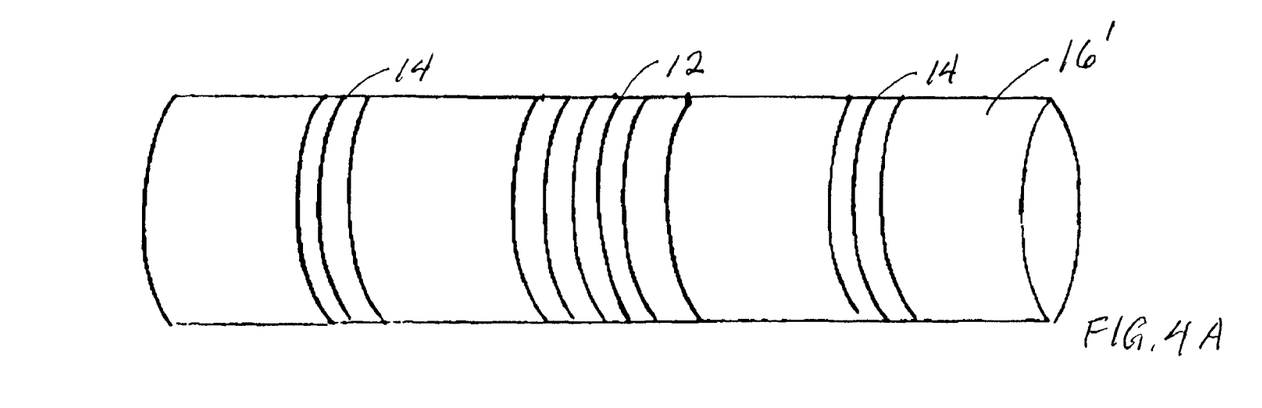
FIG. 4A is a perspective view of a source-sensor unit according to the present invention, with a solid cylindrical coil form.
Figure 4B:
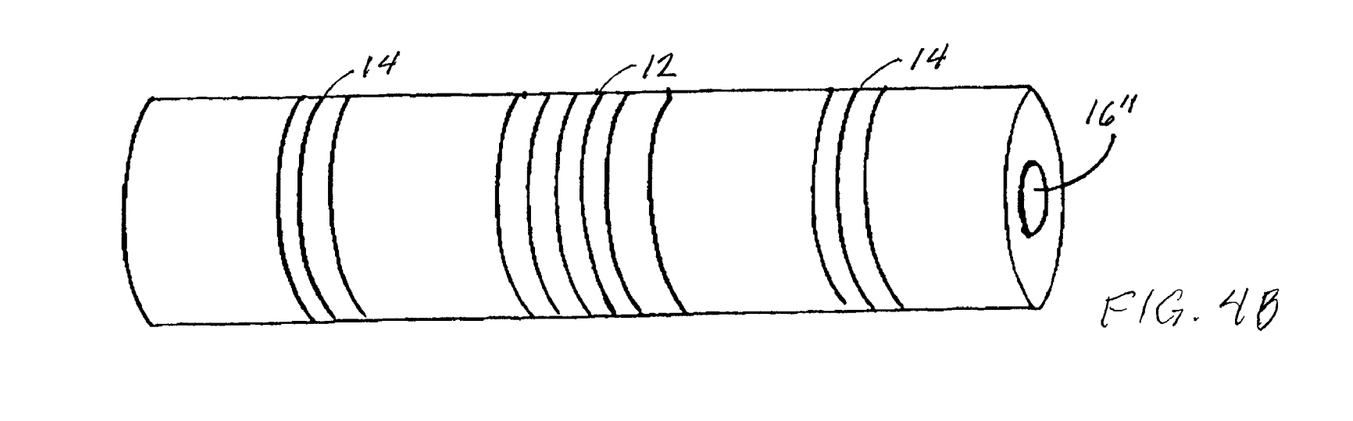
FIG. 4B is a perspective view of a source-sensor unit according to the present invention, with a thick walled cylindrical coil form.

Minimizing temperature variations. In addition to making the source-sensor unit insensitive to temperature variations, one can also minimize thermal drifts by taking steps to minimize the temperature variations themselves. One method of minimizing temperature variations is to put the structure comprising the magnetic sensors and magnetic field sources into thermal contact with a sufficiently large thermal mass to ensure that any significant temperature variations occur on a time scale much longer than that required by the magnetic susceptibility measurement itself. The presence of a large thermal mass retards any temperature variations, so that they occur on a time-scale much slower than that of the desired magnetic susceptibility measurement. For example, in the type of sensor configuration shown in FIG. 1, one way to provide a large thermal mass is to make the coil form 16 of considerable mass as a solid cylinder, or, alternatively, as a thick-walled hollow cylinder, as shown in FIGS. 4A and 4B. In FIG. 4A, an applied field coil 12 and two sensor coils 14 are wound on a solid cylindrical coil form 16'. The applied field coil 12 and the sensor coils 14 can be copper wires set in grooves on the surface of the coil form 16'. In FIG. 4B, an applied field coil 12 and two sensor coils 14 are wound on a thick walled hollow cylindrical coil form 16". Here again, the applied field coil 12 and the sensor coils 14 can be copper wires set in grooves on the surface of the coil form 16".

In addition, temperature variations can be reduced by suitably insulating the source-sensor unit from ambient temperature variations and/or by shielding it from shifting air currents in the room. If the source-sensor unit is insulated in this manner, and if the applied magnetic field is produced using field coils, as opposed to a permanent magnet, it is necessary to remove the heat produced by ohmic losses in the field coils. One way to remove this heat, without introducing unwanted temperature variations, is to provide a thermal link to the outside world, and to provide a point external to the shield or insulation at which the temperature can be controlled, thereby minimizing temperature fluctuations in the source-sensor unit. Active feedback can be utilized to stabilize temperature fluctuations. Temperature stabilization can also be achieved by putting the thermal link in contact with a large thermal mass.

Another way to enhance temperature stability, and thereby to control the temperature, is to put the source-sensor unit in thermal contact with an appropriate temperature-stabilizing chemical system, such as ice in water. A number of other temperature-stabilizing materials are also available, using various chemical and/or physical phase transitions, such as butanol, or tertiary-butanol, or, alternatively, other materials, or mixtures of materials. A recirculation system with a constant temperature feedback can also be employed in these configurations.

Using low-expansion material. Thermal drifts in the geometry of the source-sensor unit can be minimized by using materials with low thermal expansion coefficients in the structures that define the shapes, dimensions, and geometrical relationships of the applied-field source and the magnetic sensors. One preferred low-expansion material is quartz, which has a thermal expansion coefficient close to zero. Other preferred low-expansion materials are machinable glass-ceramic, such as MACOR™ ceramic material by Corning Glass Co., marble, sapphire, granite, or other suitable non-magnetic, electrically nonconducting materials with a low thermal expansion coefficient. These, or other available low-expansion materials, can be used in coil forms for the applied-field and sensor coils. FIGS. 4A and 4B show two sensor design embodiments in which this strategy can be employed. Low-expansion materials can also be used in other structures, such as braces or struts defining the separation and relative positions of applied-field coils and magnetic sensors.

In conjunction with the use of low thermal expansion materials, it is advantageous to provide a large thermal mass, as described above, to minimize temperature variations in the source-sensor unit.

Certain low-expansion materials, including marble, are currently known as coil form materials for some magnetic susceptibility measurements. However, the use of any low thermal expansion material in constructing a source-sensor unit specifically for ferromagnetic foreign body detection as a pre-MRI screening instrument is not currently known.

If the applied-field coils and sensor coils are made of a good electrical conductor, such as copper, the conductor will typically have a much higher thermal expansion coefficient than the low expansion materials listed above. In this case, it will be desirable to bond the conductor to the non-conductive substrate firmly, using as rigid a bonding material as possible.

The design principles disclosed above can be used in combination with ac (alternating field) or dc (constant field) magnetic susceptibility measurements, using any combination of magnetic sensors, including, for example, induction coils, magnetoresistive sensors, giant magnetoresistance sensors, spin-dependent tunneling sensors, fluxgates, single-domain fluxgates, and generating the applied field using coils, permanent magnets or coils in combination with magnetically permeable material.

Enhancing sensitivity by employing eye movements. A potential problem in ferromagnetic foreign body detection of the eye and orbit area in pre-MRI screening is that tissues in the patient's head produce their own weak magnetic susceptibility signal, which can mask the magnetic susceptibility response of the FFB. Eye movement can therefore be employed in the practice of the present invention to enhance sensitivity. By having the patient rotate his or her eyes, either randomly or in a controlled manner, modulating the orientation and/or location of the ferromagnetic foreign body is achieved. This changing orientation or position will modulate the magnetic susceptibility signal from the FFB, without substantially changing the magnetic susceptibility response of the patient's body tissues. Since the globe of the eye is nearly spherical, eye rotation will not substantially change the magnetic susceptibility signal of the eye itself. The eye may be rotated in one or two axes, such as with an up and down eye movement and/or a left and right eye movement, or in all fields of gaze within these axes, thus providing enhanced information about the particle location and orientation. If desired, repeatable eye rotations can be produced by having the patient focus on each of a series of spots or targets in turn, or having the patient track a target moving in a specific pattern.

Using a water-bag to enhance sensitivity. One problem in sensitive magnetic susceptibility measurements on the human body is the very large response due to the magnetic susceptibility contrast between the body tissues and the surrounding air. This signal varies according to the shape of the body, and this variation can mask subtle changes in the magnetic susceptibility response due to variations in the magnetic susceptibility of the tissues, or, if applicable, the presence of small ferromagnetic foreign bodies. One method to reduce the magnetic susceptibility contrast problem is to insert a deformable water bag between the patient and the sensing apparatus.

In the traditional water bag method, as commonly employed with SQUID sensor apparati, the sensing instrument is initially pressed against the patient's body. The patient is then moved away from the sensing apparatus, and the water bag is continuously supplied with water, such that the space between the sensing apparatus and the patient is filled with water at all times. With this method, the patient's body is, in effect, replaced by water throughout the field of view of the instrument, and the resulting change in magnetic susceptibility signal is due only to the difference in magnetic susceptibility between the body and water. In essence, the traditional water bag method eliminates the magnetic susceptibility signal due to the large susceptibility contrast between the water-like tissues of the body and the surrounding air.

Figure 5:
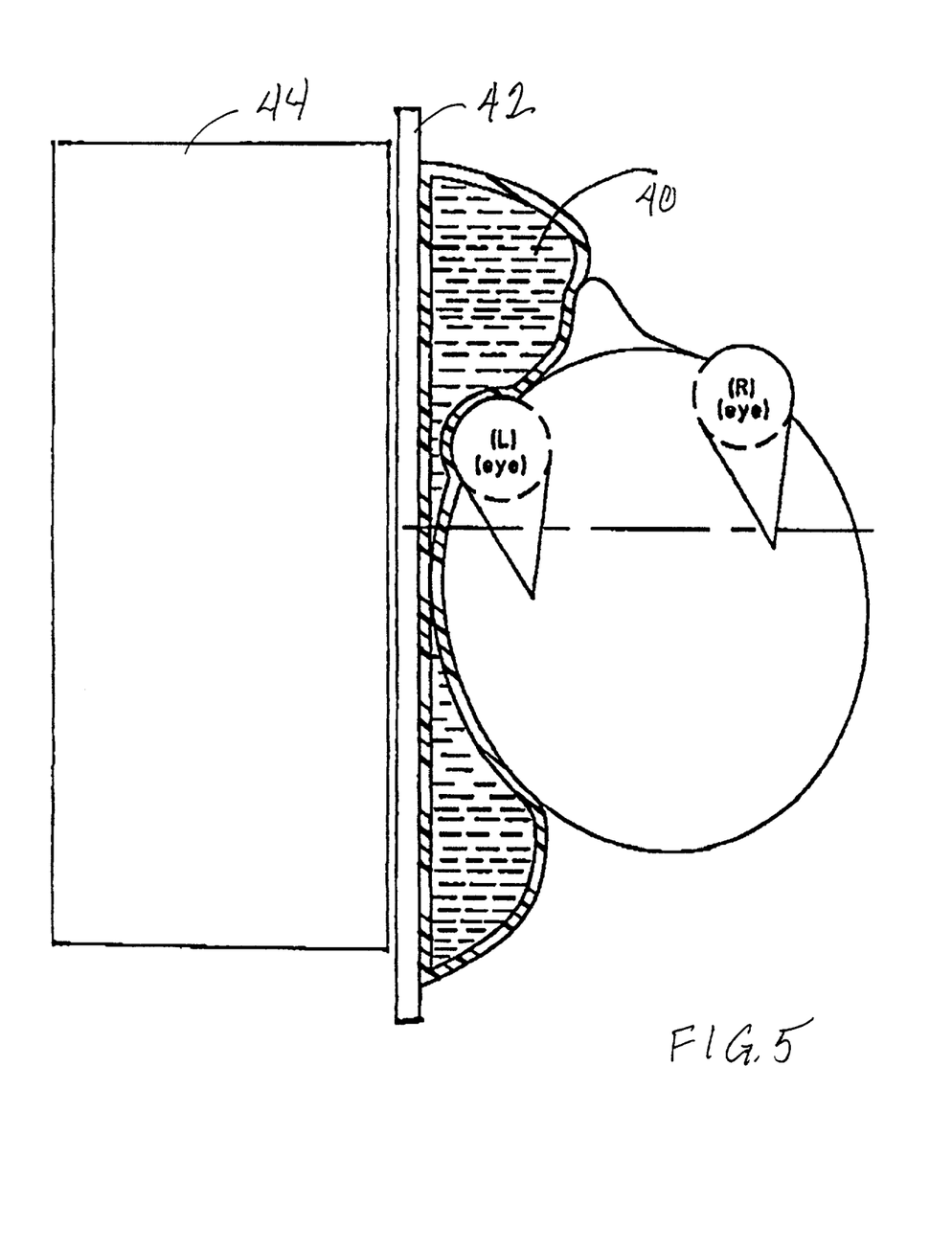
FIG. 5 is a schematic view of the apparatus of the present invention, employing a water bag.

Use of the water bag 40 in the practice of the present invention, as shown in FIG. 5, does not eliminate this air-water magnetic susceptibility contrast, but rather replaces the varying shapes of the body surface with an air-water interface of constant shape defined by a rigid, fixed barrier 42, between the water bag 40 and the source-sensor unit 44. This water bag method is very useful as a preferred embodiment when the magnetic susceptometers described above are employed in pre-MRI screening of the eye, the orbit, or the brain. The bag 40 can contain water, a water solution, a gel, or another suitable deformable material.

Using telemedicine to implement the enhanced measurements. Telemedicine can also be employed in the practice of the present invention, specifically to centralize the computer equipment with the required computational capability, thereby making the enhanced measurements widely available and facilitating quality control in the interpretation of test results. The preferred vehicle for said telemedicine is the Internet. Artificial intelligence modalities, including neural net and other expert systems, can also be employed, providing instantaneous autointerpretation of test results. Provision is made for real-time interactive feedback between the remote test instrument and a central computer processing station, thereby helping to ensure patient cooperation and reliable data acquisition.

While the present invention is fully disclosed herein, it is to be understood that this disclosure is merely illustrative of the presently preferred embodiments of the invention and that no limitations are intended other than as described in the appended claims.

We claim:

1. A method for performing pre-MRI screening for ferromagnetic foreign bodies, comprising:

providing a source-sensor unit including at least one applied-field generating element and at least one magnetic sensor;

canceling the signal due to the applied magnetic field at the location of said at least one magnetic sensor by the relative arrangement of said at least one applied-field generating element and said at least one magnetic sensor in said source-sensor unit;

generating an applied magnetic field in the eye of a patient, with said source-sensor unit;

rotating said eye, thereby moving any ferromagnetic foreign body which may be present to modulate the magnetic susceptibility signal from said ferromagnetic foreign body, without substantially changing the magnetic susceptibility response of the patient's body tissues; and generating a magnetic susceptibility measurement relevant to the presence or absence of a ferromagnetic foreign body in said eye, with said source-sensor unit.

2. The method recited in claim 1, further comprising rotating said eye in a controlled manner.

3. The method recited in claim 1, further comprising preserving said cancellation of the applied-field signal as said entire source-sensor unit expands and contracts.

* * * * *